United States Patent
Han et al.

(10) Patent No.: US 9,035,251 B2
(45) Date of Patent: May 19, 2015

(54) TERAHERTZ WAVE GENERATING MODULE AND TERAHERTZ WAVE DETECTING DEVICE INCLUDING THE SAME

(71) Applicant: ELECTRONICS AND TELECOMMUNICATIONS RESEARCH INSTITUTE, Daejeon (KR)

(72) Inventors: Sang-Pil Han, Daejeon (KR); Kyung Hyun Park, Daejeon (KR); Namje Kim, Daejeon (KR); Han-Cheol Ryu, Daejeon (KR); Jeong Woo Park, Daejeon (KR); Hyunsung Ko, Seoul (KR); Kiwon Moon, Pohang (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 56 days.

(21) Appl. No.: 14/049,059

(22) Filed: Oct. 8, 2013

(65) Prior Publication Data
US 2014/0166881 A1  Jun. 19, 2014

(30) Foreign Application Priority Data
Dec. 14, 2012  (KR) .................. 10-2012-0146850

(51) Int. Cl.
*G01J 5/20* (2006.01)
*G01N 21/3581* (2014.01)

(52) U.S. Cl.
CPC .................. *G01N 21/3581* (2013.01)

(58) Field of Classification Search
CPC .......................................... G01J 5/20
USPC ...................................... 250/338.1
See application file for complete search history.

(56) References Cited

U.S. PATENT DOCUMENTS

2010/0277726 A1* 11/2010 Logan et al. ................. 356/326

* cited by examiner

*Primary Examiner* — David Porta
*Assistant Examiner* — Hugh H Maupin

(57) ABSTRACT

A terahertz wave generating module includes a bidirectional light source which provides a first dual-mode beam in a first direction and a second dual-mode beam in a second direction; a forward lens unit which focuses the first dual-mode beam; a photomixer unit which converts the first dual-mode beam focused by the forward lens unit into a terahertz wave; a backward lens unit which focuses the second dual-mode beam; and a light output unit which uses the second dual-mode beam focused by the backward lens unit as a light signal, wherein the bidirectional light source, the forward lens unit, the photomixer unit, the backward lens unit, and the light output unit are integrated in a housing.

20 Claims, 13 Drawing Sheets

TERAHERTZ WAVE GENERATING MODULE AND TERAHERTZ WAVE DETECTING DEVICE INCLUDING THE SAME

CROSS-REFERENCE TO RELATED APPLICATIONS

This application claims priority under 35 U.S.C. §119 to Korean Patent Application No. 10-2012-0146850 filed on Dec. 14, 2012, in the Korean Intellectual Property Office, all contents of which are hereby incorporated by reference.

BACKGROUND

The inventive concept described herein relates to a terahertz wave generating module and a terahertz wave detecting device including the same.

Terahertz waves are electromagnetic waves having a frequency between that of microwaves and that of infrared light. Terahertz waves are located at the boundary between electromagnetic waves and light waves, and may have both electromagnetic and light wave characteristics. Terahertz waves may be applied to various fields such as spectroscopic material analysis, medical diagnosis, wireless local area communication, and so on.

Terahertz waves may be generated using a photomixer, a hot-hole laser, a free electron laser, and so on. When a photomixer is used, terahertz waves may be generated at room temperature, and an output frequency of the generated terahertz waves may be changed into a wide band. For such reasons, a technique of generating terahertz waves using a photomixer has been intensively researched.

However, essential elements such as a plurality of light sources, a coupler, an amplifier, and the like may be required to generate terahertz waves using a photomixer. This may cause an increase in a size of a terahertz wave generating device including such essential elements. Also, output loss may be generated by connection loss among these essential elements.

SUMMARY

One aspect of the embodiments of the inventive concept is directed to a terahertz wave generating module which comprises a bidirectional light source which provides a first dual-mode beam in a first direction and a second dual-mode beam in a second direction; a forward lens unit which focuses the first dual-mode beam; a photomixer unit which converts the first dual-mode beam focused by the forward lens unit into a terahertz wave; a backward lens unit which focuses the second dual-mode beam; and a light output unit which uses the second dual-mode beam focused by the backward lens unit as a light signal, wherein the bidirectional light source, the forward lens unit, the photomixer unit, the backward lens unit, and the light output unit are integrated in a housing.

In example embodiments, a wavelength of the second dual-mode beam is equal to that of the first dual-mode beam.

In example embodiments, the terahertz wave generating module further comprises an optical isolator located between the bidirectional light source and the forward lens unit and adjusting a propagation direction of the first dual-mode beam in one direction only.

In example embodiments, the bidirectional light source, the optical isolator, and the forward and backward lens units are formed on a support for adjusting a height according to an optical loss.

In example embodiments, the support is formed on a metal block including a thermistor for temperature measurement.

In example embodiments, the metal block is formed on a temperature pad for adjusting a temperature of the metal block.

In example embodiments, the bidirectional light source comprises a first laser bi-directionally outputting a first light of a first wavelength; and a second laser linearly integrated with the first laser and bi-directionally outputting a second light of a second wavelength.

In example embodiments, each of the first and second lasers is a DFB (Distributed Feedback) laser and the first and second lasers are integrated and connected with micro heaters for controlling the first and second wavelengths.

In example embodiments, the terahertz wave generating module further comprises a connector providing a high frequency signal to the bidirectional light source, the first dual-mode beam being modulated in response to the high frequency signal.

In example embodiments, the forward lens unit comprises a first collimation type aspherical lens converting the first dual-mode beam provided from the bidirectional light source into a collimation beam; and a second collimation type aspherical lens focusing the collimation beam on the photomixer unit.

In example embodiments, the forward lens unit comprises a focusing type aspherical lens converting the first dual-mode beam provided from the bidirectional light source into a focused beam and focusing the focused beam on the photomixer unit.

Another aspect of embodiments of the inventive concept is directed to a terahertz wave generating module which comprises a bidirectional light source which provides in a first direction a first dual-mode beam having a first wavelength and a second wavelength and provides in a second direction a first single-mode beam having the first wavelength and a second single-mode beam having the second wavelength; a forward lens unit which focuses the first dual-mode beam; a photomixer unit which converts the first dual-mode beam focused by the forward lens unit into a terahertz wave; a backward lens unit which focuses the first and second single-mode beams; and an optical detection unit which detects the first and second single-mode beams focused by the backward lens unit, wherein the bidirectional light source, the forward lens unit, the photomixer unit, the backward lens unit, and the optical detection unit are integrated in a housing.

In example embodiments, the bidirectional light source comprises a first laser integrated on a first node of a Y-branch type waveguide and bi-directionally outputting the first single-mode beam having the first wavelength; and a second laser integrated on a second node of the Y-branch type waveguide and bi-directionally outputting the second single-mode beam having the second wavelength, wherein the first and second single-mode beams are coupled at a third node of the Y-branch type waveguide to be output as the first dual-mode beam.

In example embodiments, a Y-branch type waveguide connected with the third node is integrated into two waveguides, the first dual-mode beam being output through the two waveguides.

In example embodiments, the optical detection unit comprises an optical filter pair filtering the first and second single-mode beams; and an optical detector pair detecting the filtered first and second single-mode beams.

In example embodiments, the photomixer unit comprises a photomixer chip including at least one electrode pad and generating a terahertz wave in response to a beam; a submount including at least one solder pad for supplying electric power to the electrode pad and fixing the photomixer chip; a coaxial cable connected with the solder pad of the submount; a photomixer body fixing the photomixer chip, the submount and the coaxial cable and emitting heat generated from the photomixer chip; and a silicon lens attached to the photomixer body and controlling a direction of the terahertz wave.

In example embodiments, the photomixer chip comprises an active layer generating a photocurrent in response to the beam; and an antenna emitting a terahertz wave in response to the photocurrent.

Still another aspect of embodiments of the inventive concept is directed to a terahertz wave detecting device which comprises a terahertz wave generating module which provides in a first direction a terahertz wave of first and second wavelengths and provides in a second direction a dual-mode light signal corresponding to the terahertz wave, the terahertz wave and the light signal being modulated in response to a high frequency signal; a monitoring module which monitors the dual-mode light signal; and a detection module which detects the terahertz wave using the dual-mode light signal.

In example embodiments, the monitoring module comprises at least one optical filter having different filter characteristics with respect to the first wavelength and the second wavelength; and at least one optical detector detecting a light passing through the optical filter to monitor the dual-mode light signal.

In example embodiments, the detection module comprises an optical delay line delaying the dual-mode light signal in response to a phase of the terahertz wave; an optical amplifier amplifying the delayed dual-mode light signal; and a detector detecting the terahertz wave via homodyne detection using the amplified dual-mode light signal.

BRIEF DESCRIPTION OF THE FIGURES

The above and other objects and features will become apparent from the following description with reference to the following figures, wherein like reference numerals refer to like elements throughout the figures unless otherwise specified, and wherein.

DETAILED DESCRIPTION

Figure 1:
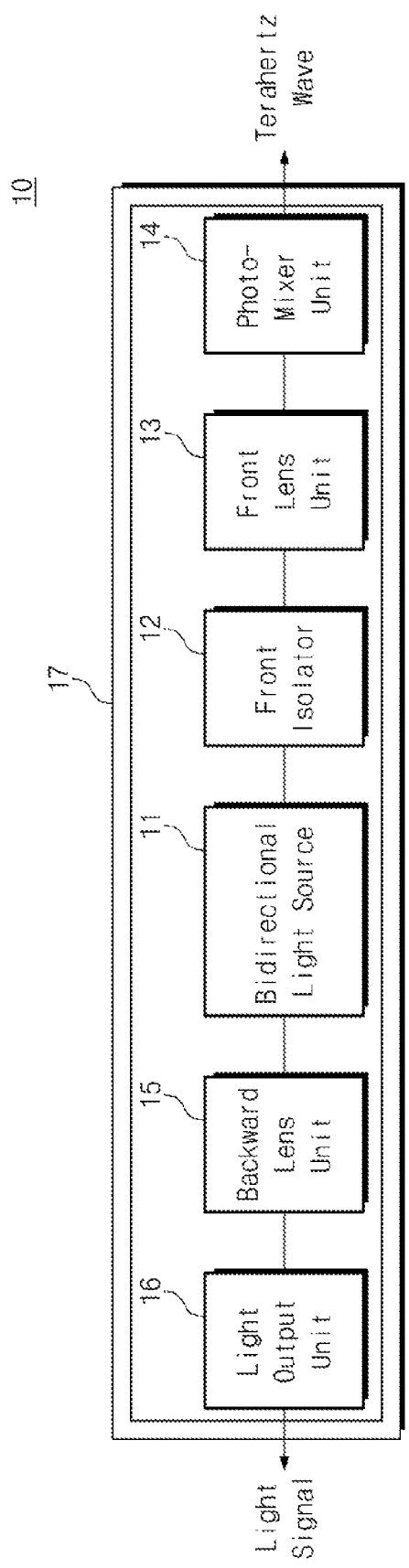
FIG. 1 is a block diagram schematically illustrating a terahertz wave generating module according to an embodiment of the inventive concept.

Embodiments of the inventive concept will be described in detail with reference to the accompanying drawings. The inventive concept, however, may be embodied in different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus, descriptions thereof will be presented only once. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer, or section from another region, layer, or section. Thus, a first element, component, region, layer, or section could be termed a second element, component, region, layer, or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation above and below. The device may be otherwise oriented (rotated by 90 degrees or other angles) and the spatially relative descriptors used herein interpreted accordingly.

In addition, it will also be understood that when a layer is referred to as being "between" two layers, only this layer can be between the two layers, or one or more intervening layers may also be present.

The terminology used herein is for the purpose of describing particular embodiments only and is not intended to limit the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having meanings consistent with their meanings in the context of the relevant art and/or the present specification and will not be interpreted in an idealized or overly formal sense unless expressly so defined herein.

FIG. 1 is a block diagram schematically illustrating a terahertz wave generating module according to an embodiment of the inventive concept. Referring to FIG. 1, a terahertz wave generating module 10 may include a bidirectional light source 11, a forward isolator 12, a forward lens unit 13, a photomixer unit 14, a backward lens unit 15, a light output unit 16, and a housing unit 17.

The terahertz wave generating module 10 may provide, using the bidirectional light source 11 bi-directionally providing a dual-mode beam, a terahertz wave and a light signal having a frequency corresponding to the terahertz wave. The terahertz wave generating module 10 may monitor or detect the terahertz wave using the light signal.

The bidirectional light source 11 may provide a light forward and backward. A light provided from the bidirectional light source 11 may be a dual-mode beam. The bidirectional light source 11 may be a DFB (Distributed Feedback) dual-mode laser. The bidirectional light source 11 will be more fully described with reference to FIG. 2.

The forward isolator 12 may prevent a forward beam provided from the bidirectional light source 11 from being reflected and returning to the bidirectional light source 11. The forward isolator 12 may a polarizer. However, the inventive concept is not limited thereto. The forward isolator 12 may transfer the forward beam to the forward lens unit 13.

The forward lens unit 13 may focus the forward beam provided from the forward isolator 12. The forward lens unit 13 may include aspherical lenses having various shapes and a support for adjusting a height of an aspherical lens. The forward lens unit 13 will be more fully described with reference to FIGS. 3 and 4. The forward lens unit 13 may send the focused forward beam to the photomixer unit 14.

The photomixer unit 14 may output a terahertz wave in response to the forward beam provided from the forward lens unit 13. The photomixer unit 14 may include a photomixer chip and a lens. The photomixer unit 14 will be more fully described with reference to FIG. 7.

When the forward beam is incident on the photomixer chip, electron-hole pairs may be generated through absorption of the incident forward beam. The electron-hole pairs thus generated may be accelerated by an external bias voltage to generate a photocurrent. A frequency of a terahertz wave generated by the photocurrent may be decided according to a beating frequency of the provided forward beam.

Since a forward beam is a dual-mode beam, the forward beam may be generated by mixing a light having a first frequency and a light having a second frequency. In the photomixer chip, a photocurrent having a third frequency corresponding to a difference between the first frequency and the second frequency may be generated by an interference phenomenon between the lights having different frequencies. An electromagnetic wave having the third frequency, that is, a terahertz wave, may be emitted according to the generated photocurrent.

The backward lens unit 15 may focus a backward beam provided from the bidirectional light source 11. The backward lens unit 15 may include aspherical lenses having various shapes and a support for adjusting a height of an aspherical lens. The backward lens unit 15 may send the focused backward beam to the light output unit 16.

The light output unit 16 may output a backward beam provided from the backward lens unit 15 as a light signal. The light output unit 16 may include a backward isolator for preventing a backward beam from being reflected and returning thereto. The light output unit 16 may include an optical fiber assembly for reducing loss generated when a light signal is transferred to an external optical component (e.g., an optical fiber). The light output unit 16 will be more fully described with reference to FIG. 5.

The above-described terahertz wave generating module 10 may simultaneously provide a terahertz wave and a light signal having a frequency corresponding to the terahertz wave by using the bidirectional light source 11. The terahertz wave generated from the terahertz wave generating module 10 may be monitored using the light signal. Also, the terahertz wave generated from the terahertz wave generating module 10 may be detected via homodyne detection using the light signal having the same frequency.

The above-described inner components, that is, the bidirectional light source 11, the forward isolator 12, the forward lens unit 13, the photomixer unit 14, the backward lens unit 15, and the light output unit 16, may be formed on a metal block. The housing unit 17 may fix the above-described inner components and the metal block. Also, the housing unit 17 may include wirings for providing a bias voltage and a power supply voltage to the inner components. A detailed arrangement of the inner components and the housing unit 17 will be more fully described with reference to FIG. 5.

As described above, the terahertz wave generating module 10 may be provided in the housing unit 17 in a fixed state. The terahertz wave generating module 10 may have a small size. Since a connection loss between the inner components may be small, the efficiency of the terahertz wave generating module 10 may be excellent.

Figure 2:
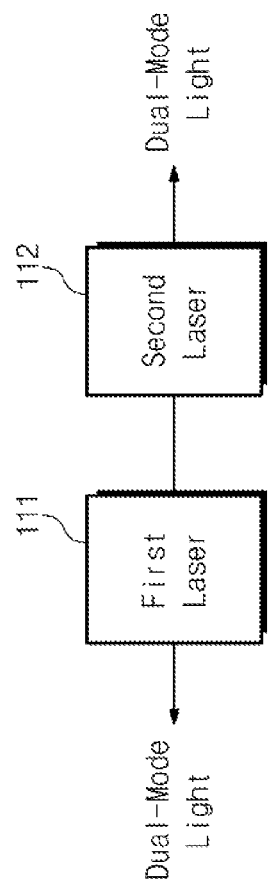
FIG. 2 is a block diagram schematically illustrating a bidirectional light source according to an embodiment of the inventive concept.

FIG. 2 is a block diagram schematically illustrating a bidirectional light source according to an embodiment of the inventive concept. Referring to FIG. 2, a bidirectional light source 110 may include a first laser 111 and a second laser 112.

The first and second lasers 111 and 112 may each be a DFB laser. The first and second lasers 111 and 112 may be collinearly integrated. The first laser 111 may provide a first light having a first wavelength. The second laser 112 may provide a second light having a second wavelength.

A phase adjustment area may be formed between the first laser 111 and the second laser 112. Since the first and second lasers 111 and 112 are collinearly integrated, the first light and the second light may interfere with each other. The phase adjustment area may adjust phases of the first and second lights to adjust an interference characteristic between the first light and the second light.

Each of the first and second lasers 111 and 112 may be integrated and connected with a micro heater. A wavelength of a semiconductor laser may vary with temperature. Thus, the first wavelength and the second wavelength may be controlled by adjusting a temperature through the micro heaters.

The above-described bidirectional light source 110 may sequentially bi-directionally provide a light having a stable dual mode (a first wavelength mode and a second wavelength mode). Also, it is possible to control a wavelength of a dual-mode beam provided from the bidirectional light source 110 to have a required value by using the micro heaters.

Figure 3:
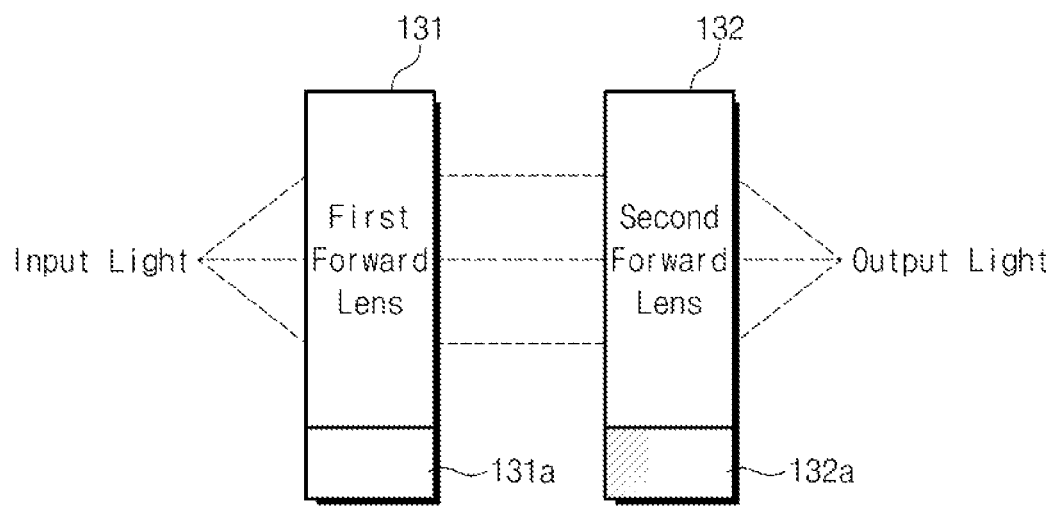
FIG. 3 is a block diagram schematically illustrating a forward lens unit according to an embodiment of the inventive concept.

FIG. 3 is a block diagram schematically illustrating a forward lens unit according to an embodiment of the inventive concept. Referring to FIG. 3, a forward lens unit 130 may include a forward lens 131, a first forward lens support 131a, a second forward lens 132, and a second forward lens support 132b.

The first and second forward lenses 131 and 132 may each be a collimation type aspherical lens. The forward lens 131 may convert an input forward beam into a collimation beam. The second forward lens 132 may again focus a forward beam incident thereon in parallel toward a focus on a photomixer unit 14 (refer to FIG. 1).

The forward lens 131 may be placed on the first forward lens support 131a. The second forward lens 132 may be placed on the second forward lens support 132a. The first forward lens support 131a and the second forward lens support 132a may adjust heights of the forward lens 131 and the second forward lens 132. Optical coupling of the first and second forward lenses 131 and 132 may be adjusted using the first forward lens support 131a and the second forward lens support 132a.

The forward lens unit 130 may transfer with small loss a forward beam provided from a forward isolator 12 (refer to FIG. 1) to the photomixer unit 14 by using a plurality of forward lenses and forward lens supports.

Figure 4:
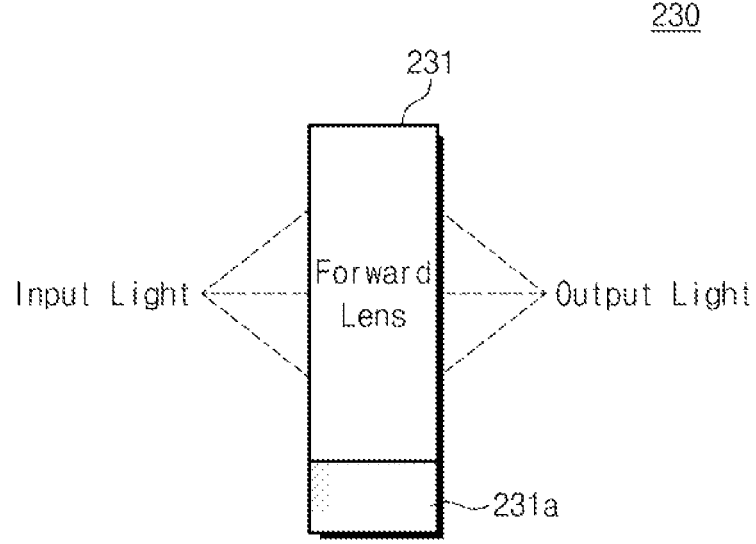
FIG. 4 is a block diagram schematically illustrating a forward lens unit according to another embodiment of the inventive concept.

FIG. 4 is a block diagram schematically illustrating a forward lens unit according to another embodiment of the inventive concept. Referring to FIG. 4, a forward lens unit 230 may include a forward lens 231 and a forward lens support 231a.

The forward lens 231 may be a focusing type aspherical lens. The forward lens 231 may focus an input forward beam toward a focus on a photomixer unit 14 (refer to FIG. 1). The forward lens 231 may be placed on the forward lens support 231a. The forward lens support 231a may adjust a height of the forward lens 231.

The above-described forward lens unit 230 may transfer with small loss a forward beam provided from a forward isolator 12 (refer to FIG. 1) to the photomixer unit 14 by using the forward lens 231 and the forward lens support 231a.

Figure 5:
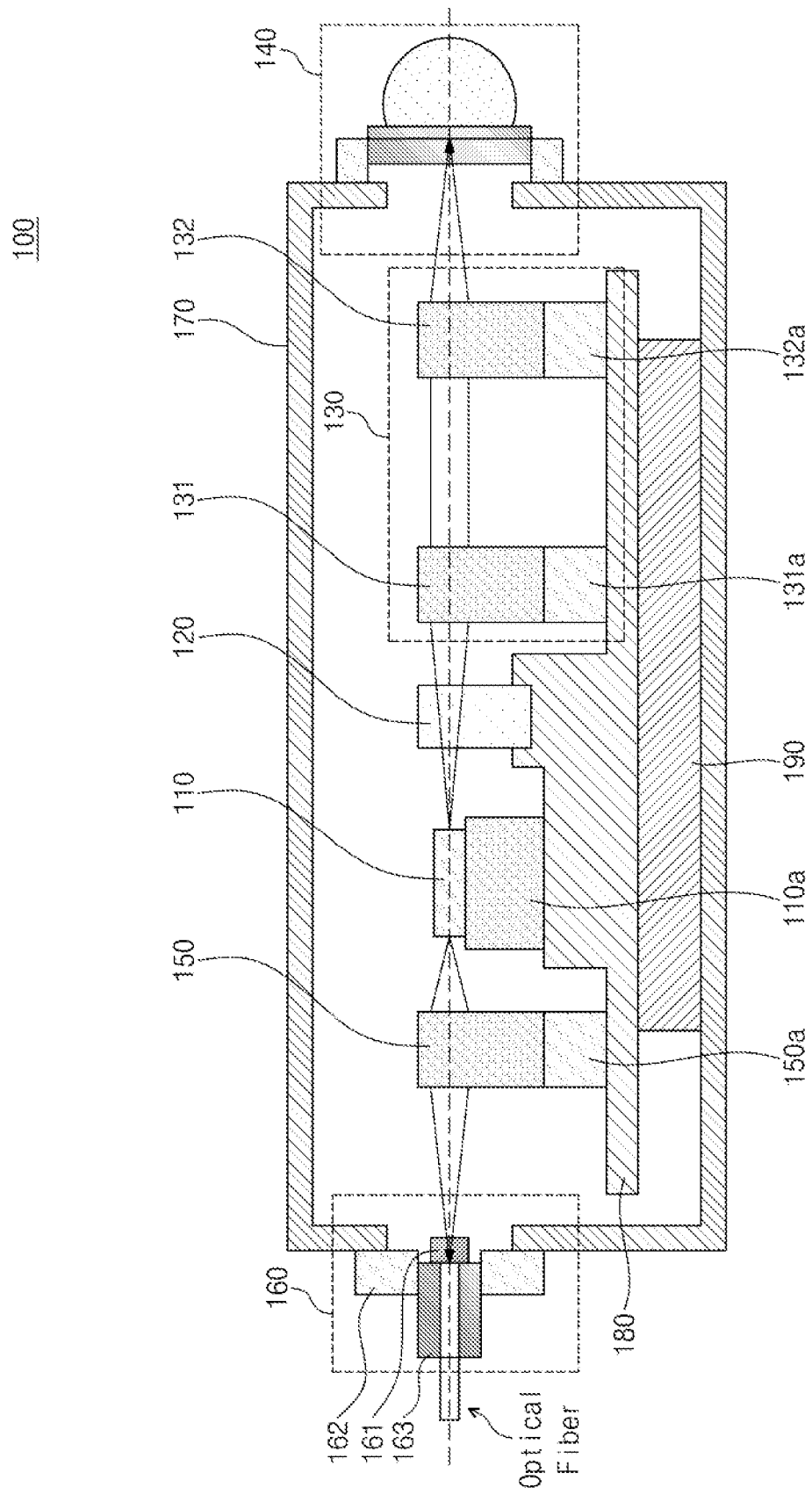
FIG. 5 is a diagram schematically illustrating a terahertz wave generating module including the forward lens unit of FIG. 3.

FIG. 5 is a diagram schematically illustrating a terahertz wave generating module including the forward lens unit of FIG. 3. Referring to FIG. 5, a terahertz wave generating module 100 may include a bidirectional light source 110, a light source submount 110a, a forward isolator 120, a forward lens unit 130, a photomixer unit 140, a backward lens unit 150, a light output unit 160, a housing 170, a metal block 180, and a temperature pad 190. The bidirectional light source 110, the forward isolator 120, the photomixer unit 140, the backward lens unit 150, and the housing 170 may be substantially the same as the bidirectional light source 11, the forward isolator 12, the photomixer unit 14, the backward lens unit 15, and the housing 17 of FIG. 2. The forward lens unit 130 of FIG. 5 may be substantially the same as the forward lens unit 130 of FIG. 3.

The bidirectional light source 110 may be formed on the light source submount 110a. The light source submount 110a may include a wiring for providing electric power to the bidirectional light source 110. Also, the light source submount 110a may dissipate heat generated by the bidirectional light source 110.

The light source submount 110a may include AlN (Aluminum Nitride). Since the heat conductivity of AlN is high, heat may be efficiently dissipated.

The light output unit 160 may include a backward isolator 161, an optical fiber connection rod 162, and an optical fiber assembly 163. The light output unit 160 may output a backward beam provided from the backward lens unit 150 as a light signal.

The backward isolator 161 may prevent a backward beam provided from the backward lens unit 150 from being reflected and returning the backward lens unit 150. The backward isolator 161 may be a polarizer. However, the inventive concept is not limited thereto.

The optical fiber connection rod 162 may have a rod shape structure for supporting an external optical part (e.g., an optical fiber). The optical fiber assembly 163 may have a structure for enabling a backward beam to be easily connected with an optical fiber.

The light output unit 160 may have an optical interconnection function such that a backward beam provided from the backward lens unit 150 may be easily transferred to an external optical part.

The forward isolator 120, the forward lens unit 130, and the backward lens unit 150 may be placed on the metal block 180. The metal block 180 may include a thermistor for sensing a temperature.

The temperature pad 190 may include a thermo electric cooler (TEC). The temperature pad 190 may control heat transmitted from the metal block 180 to control a temperature of the bidirectional light source 110.

The above-described terahertz wave generating module 100 may simultaneously provide a terahertz wave and a light signal having a frequency corresponding to the terahertz wave by using the bidirectional light source 110. The terahertz wave generated from the terahertz wave generating module 100 may be monitored using the light signal. Alternatively, the terahertz wave generated from the terahertz wave generating module 100 may be detected via homodyne detection using the light signal having the same frequency.

Also, since the terahertz wave generating module 100 may be integrated in the housing 170, it may have a small size. The terahertz wave generating module 100 may include the photomixer unit 140 and the light output unit 160 for an easy optical interconnection with an external device.

Figure 6:
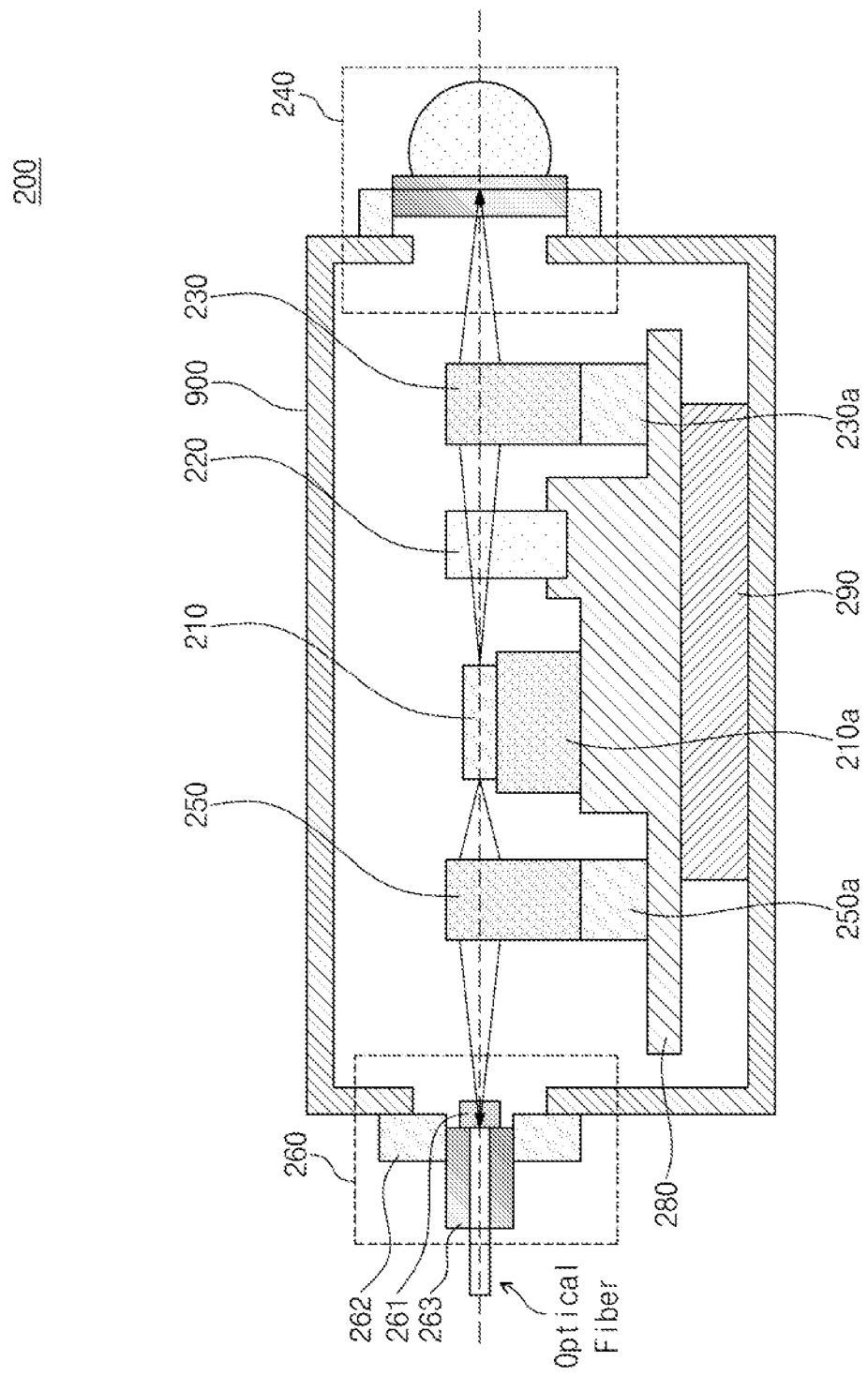
FIG. 6 is a diagram schematically illustrating a terahertz wave generating module including the forward lens unit of FIG. 4 according to an embodiment of the inventive concept.

FIG. 6 is a diagram schematically illustrating a terahertz wave generating module 200 including the forward lens unit of FIG. 4 according to an embodiment of the inventive concept. The terahertz wave generating module 200 of FIG. 6 may be substantially the same as the terahertz wave generating module 100 of FIG. 5 except for a forward lens unit 230.

The forward lens unit 230 may include a forward lens 231 and a forward lens support 231a. The forward lens 231 may be a focus type aspherical lens. The forward lens 231 may focus an input forward toward a focus on the photomixer unit 240. The forward lens support 231*a* may adjust a height of the forward lens 231.

The forward lens unit 230 may transfer with small loss a forward beam provided from a forward isolator 220 to the photomixer unit 240 by using the forward lens 231 and the forward lens support 231*a*. Thus, the terahertz wave generating module 200 may generate a terahertz wave with small loss.

Figure 7:
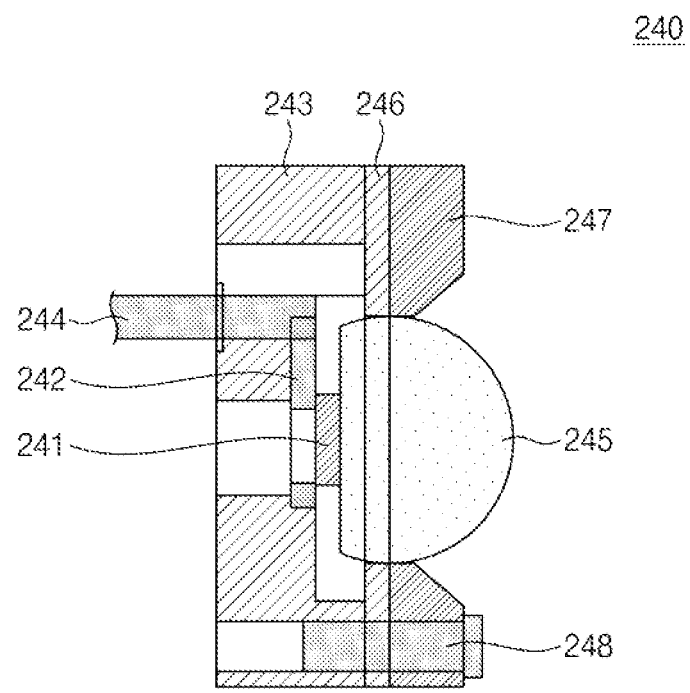
FIG. 7 is a diagram schematically illustrating a photomixer unit of FIG. 6 according to an embodiment of the inventive concept.
Figure 8:
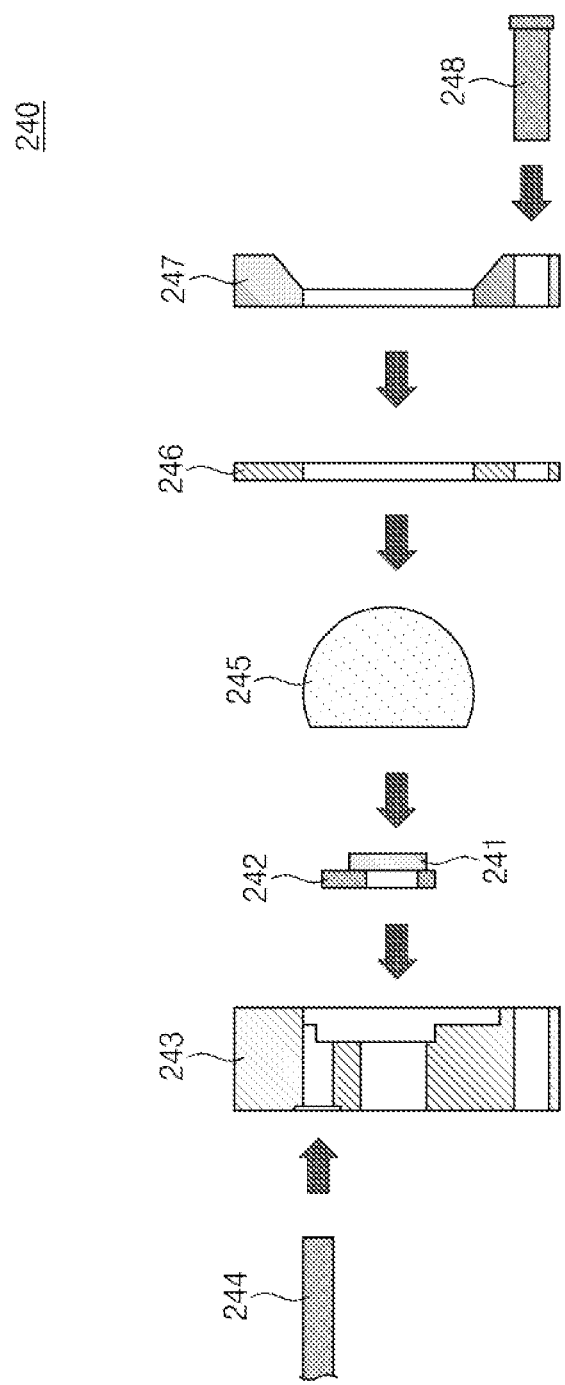
FIG. 8 is a diagram schematically illustrating a method of connecting elements of the photomixer unit of FIG. 7.

FIG. 7 is a diagram schematically illustrating the photomixer unit 240 of FIG. 6 according to an embodiment of the inventive concept. FIG. 8 is a diagram schematically illustrating a method of connecting elements of the photomixer unit 240 of FIG. 7. The photomixer unit 240 may include a photomixer chip 241, a photomixer submount 242, a photomixer body 243, a mini coaxial cable 244, a silicon lens 245, a urethane ring 246, a photomixer cover 247, and bolt 248.

The photomixer chip 241 may include an antenna and an active layer for terahertz wave generation. The photomixer chip 241 may include at least one electrode pad for receiving a bias voltage. When a light is applied to the active layer of the photomixer chip 241, optical carriers may be generated in the active layer. At this time, the antenna may emit a terahertz wave.

The photomixer submount 242 may be flip-chip bonded with the photomixer chip 241. The photomixer submount 242 may include at least one or more solder pads connected with an electrode pad of the photomixer chip 241. The photomixer submount 242 may be fixed to the photomixer body 243.

The mini coaxial cable 244 may be attached to the photomixer submount 242 through the photomixer body 243. The mini coaxial cable 244 may be connected with the solder pad of the photomixer submount 242. The silicon lens 245 may be connected with a bottom surface of the photomixer chip 241. The silicon lens 245 may be fixed to the photomixer body 243 by the urethane ring 246, the photomixer cover 247 and the bolt 248.

The photomixer body 243 may support the photomixer submount 242, the mini coaxial cable 244, and the silicon lens 245. The photomixer body 243 may emit heat generated from the active layer of the photomixer chip 241.

The photomixer unit 240 may be connected with a housing 270 (refer to FIG. 6) to convert a forward beam from the forward lens unit 230 (refer to FIG. 6) into a terahertz wave.

Figure 9:
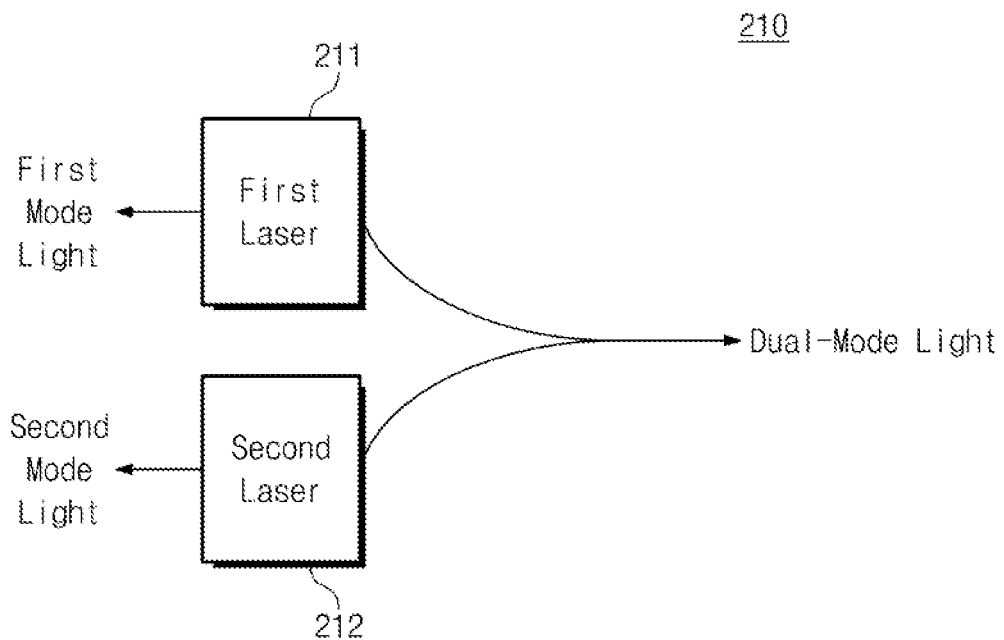
FIG. 9 is a block diagram schematically illustrating a bidirectional light source according to another embodiment of the inventive concept.

FIG. 9 is a block diagram schematically illustrating a bidirectional light source 210 according to another embodiment of the inventive concept. Referring to FIG. 9, the bidirectional light source 210 may provide lights forward and backward. The bidirectional light source 210 may provide a dual-mode beam forward and a single-mode beam backward.

The bidirectional light source 210 may include a first laser 211 and a second laser 212. The first and second lasers 211 and 212 may each be a DFB laser. The first and second lasers 211 and 212 may be integrated on a Y-branch type line. The first laser 211 may provide a first mode beam having a first wavelength and the second laser 212 may provide a second mode beam having a second wavelength.

Micro heaters may be integrated in the first and second lasers 211 and 212, respectively. A wavelength of a semiconductor laser may vary with temperature. Thus, the first and second wavelengths may be controlled by temperature adjustment through the micro heaters.

As illustrated in FIG. 9, the first and second lasers 211 and 212 may be integrated at first and second nodes of a Y-branch type line. Thus, the first and second mode beams generated from the first and second lasers 211 and 212 may be combined such that a dual-mode beam is output forward. Also, the first and second mode beams generated from the first and second lasers 211 and 212 may be output backward as two lights each having a single mode.

Figure 10:
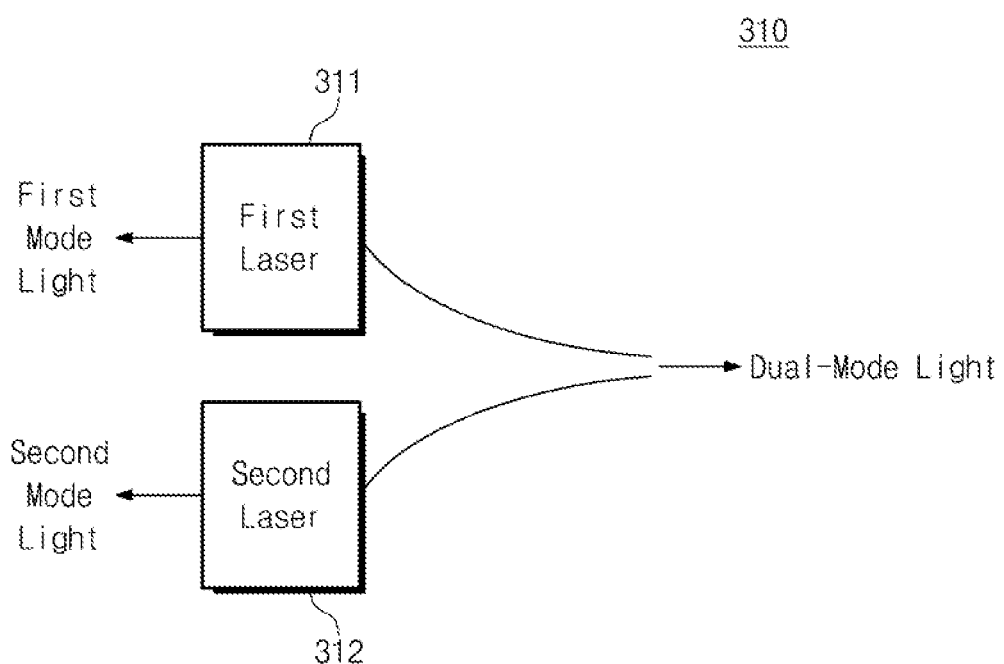
FIG. 10 is a block diagram schematically illustrating a bidirectional light source according to still another embodiment of the inventive concept.

FIG. 10 is a block diagram schematically illustrating a bidirectional light source 310 according to still another embodiment of the inventive concept. Referring to FIG. 10, the bidirectional light source 310 may include a first laser 311 and a second laser 312. The bidirectional light source 310 of FIG. 10 may be substantially the same as the bidirectional light source 210 of FIG. 9 except for a shape of a Y-branch type line.

In FIG. 10, a Y-branch type waveguide may be formed of two waveguides connected to a third node. The waveguides may be optical waveguides. The waveguides may not contact each other. However, the waveguides may be closely disposed such that lights passing through the waveguides interfere with each other. A dual-mode beam may be output by interference of lights passing through the waveguides. Thus, the bidirectional light source 310 of FIG. 10 may provide a dual-mode beam forward and a single-mode beam backward. Also, the bidirectional light source 310 may provide a dual-mode beam using two waveguides, so that output loss is reduced compared with the case where a waveguide is used.

Figure 11:
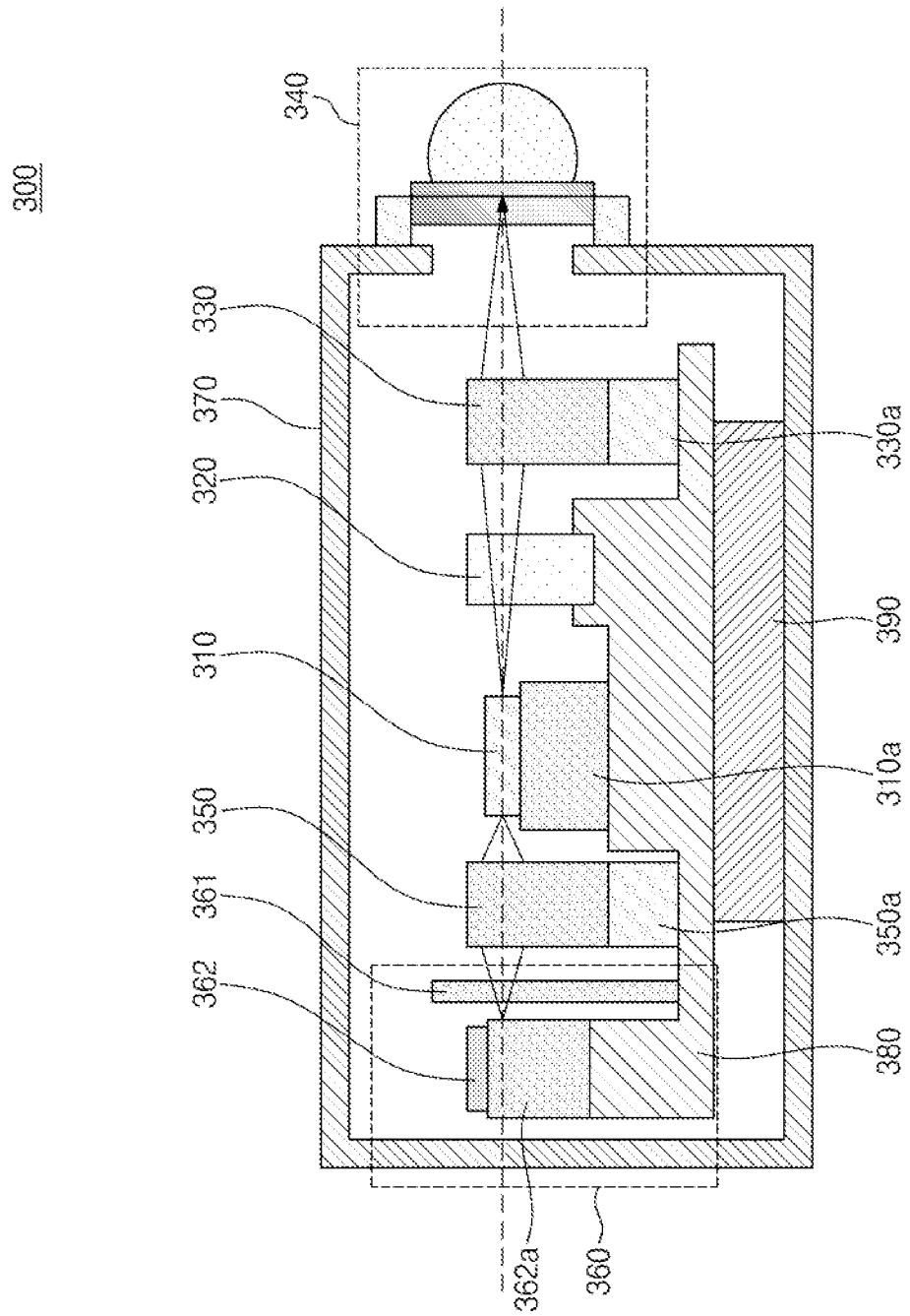
FIG. 11 is a diagram schematically illustrating a terahertz wave generating module including a forward lens unit of FIG. 9 or 10.

FIG. 11 is a diagram schematically illustrating a terahertz wave generating module 300 including a bidirectional light source as shown in FIG. 9 or 10. Referring to FIG. 11, the terahertz wave generating module 300 may include a bidirectional light source 310, a light source submount 310*a*, a forward isolator 320, a forward lens unit 330, a photomixer unit 340, a backward lens unit 350, an optical detection unit 360, a housing 370, a metal block 380, and a temperature pad 390.

The bidirectional light source 310 may provide a dual-mode beam forward and two single-mode beams backward. A forward beam generated from the bidirectional light source 310 may be output as a terahertz wave through the forward isolator 320, the forward lens unit 330, and the photomixer unit 340.

A backward beam generated at the bidirectional light source 310 may be transmitted to the optical detecting unit 360 through the backward lens unit 350. The optical detection unit 360 may include an optical filter pair 361, an optical detector pair 362, and an optical detector pair support 362*a*.

The optical filter pair 361 may filter a backward beam provided from a backward lens unit 350. The optical filter pair 361 may include two optical filters. The optical filter pair 361 may filter two single-mode beams included in the backward beam by using two optical filters.

The optical detector pair 362 may include two optical detectors. The optical detector pair 362 may detect two single-mode beams filtered by the optical filter pair 361. The optical detector pair 362 may be formed on the optical detector pair support 362*a*.

The optical detector pair support 362*a* may adjust a height of the optical detector pair 362 such that the optical filter pair 361 and the optical detector pair 362 are easily photo coupled.

The terahertz wave generating module 300 may provide a terahertz wave forward by using a bidirectional light source and detect two light signals having an opposite frequency to a beating frequency. Also, since the terahertz wave generating module 300 is integrated in the housing 370, the terahertz wave generating module 300 may have a small area. The terahertz wave generating module 300 may include the photomixer unit 340 and the optical detection unit 360 and be easily photo coupled with an external device.

Figure 12:
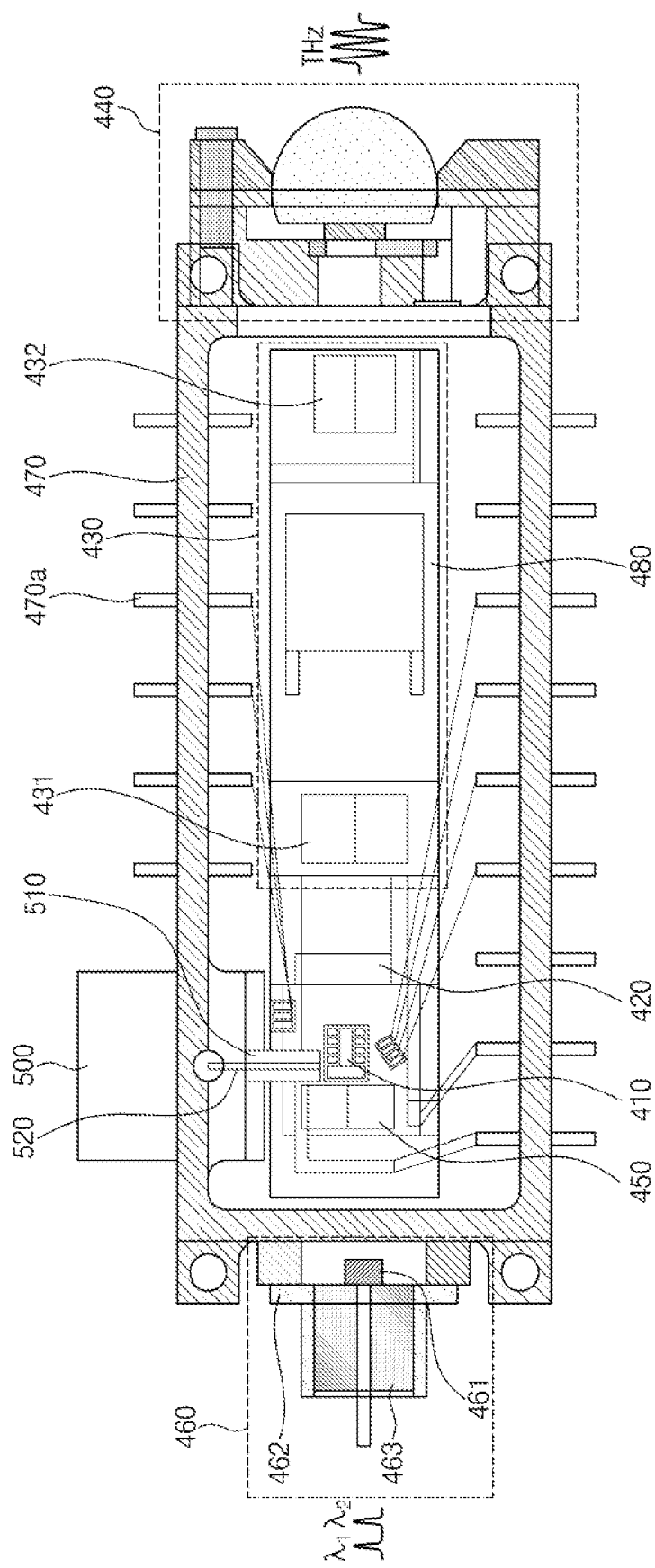
FIG. 12 is a plan view of the terahertz wave generating module of FIG. 5.

FIG. 12 is a plan view of the terahertz wave generating module 400 of FIG. 5. Referring to FIG. 12, the terahertz wave generating module 400 may include a bidirectional light source 410, a forward isolator 420, a forward lens unit 430, a photomixer unit 440, a backward lens unit 450, a light output unit 460, a housing 470, a metal block 480, a connector 500, a micro stripe line 510, and a connector center electrode 520. The bidirectional light source 410, the forward isolator 420, the forward lens unit 430, the photomixer unit 440, the backward lens unit 450, and the light output unit 460 may be substantially the same as the bidirectional light source 110, the forward isolator 120, the forward lens unit 130, the photomixer unit 140, the backward lens unit 150, and the light output unit 160 of FIG. 5.

The bidirectional light source 410 may be connected with the connector 500 through the micro stripe line 510 and the connector center electrode 520. The connector 500 may provide a high frequency signal from an external device to the bidirectional light source 410.

The connector 500 may be a coaxial connector. The connector 500 may be a K-connector. However, the inventive concept is not limited thereto. The connector 500 may provide the high frequency signal for high speed modulation of a light generated by the bidirectional light source 410. The micro stripe line 510 may match a characteristic impedance between the bidirectional light source 410 and the connector center electrode 520 connected with the connector 500.

The housing 470 may include a plurality of pines 470a for supplying electric power to constituent elements. A pin shape and the number of pines illustrated in FIG. 12 may be exemplary. The inventive concept is not limited thereto. Each pin may be connected with an external electrode to provide electric power or a signal to a terahertz wave generating module 400.

The terahertz wave generating module 400 may provide a terahertz wave forward by using a bidirectional light source and detect two light signals having an opposite frequency to that of the backward terahertz wave. The terahertz wave provided by the terahertz wave generating module 400 may be modulated in response to a high frequency signal provided from the connector 500.

Also, as the terahertz wave generating module 400 is integrated in the housing 470, the terahertz wave generating module 400 may have an efficient wiring structure within a small area. The terahertz wave generating module 400 may include a photomixer unit 440 and the optical detection unit 460 to be easily photo coupled with an external device.

Figure 13:
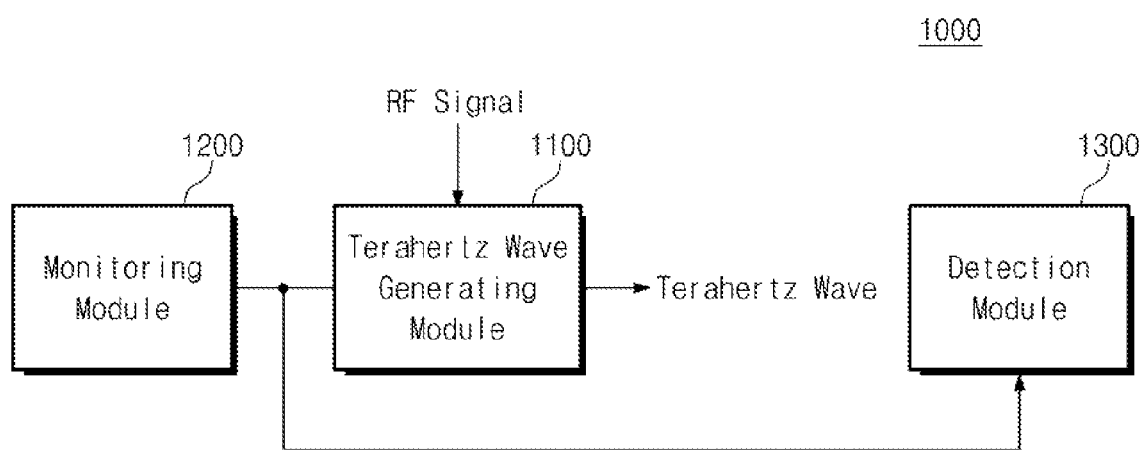
FIG. 13 is a block diagram schematically illustrating a terahertz wave detecting device including a terahertz wave generating module of the inventive concept.

FIG. 13 is a block diagram schematically illustrating a terahertz wave detecting device 1000 including a terahertz wave generating module 1100 of the inventive concept. Referring to FIG. 13, the terahertz wave detecting device 1000 may further include a monitoring module 1200 and a detection module 1300.

The terahertz wave generating module 1100 may simultaneously provide a terahertz wave and a light signal having a frequency corresponding to the terahertz wave by using a bidirectional light source. The terahertz wave and the light signal provided from the terahertz wave generating module 1100 may be modulated in response to an RF signal provided from an external device. The terahertz wave generated by the terahertz wave generating module 1100 may be output to a target location. The light signal generated by the terahertz wave generating module 1100 may be provided to the monitoring module 1200 and the detection module 1300.

The monitoring module 1200 may monitor the light signal. The monitoring module 1200 may analyze a wavelength of the light signal. The monitoring module 1200 may include a plurality of optical filters and a plurality of optical detectors. Information associated with the light signal analyzed by the monitoring module 1200 may be fed back to the terahertz wave generating module 1100.

The detection module 1300 may detect the terahertz wave generated by the terahertz wave generating module 1100 via homodyne detection using the light signal. The detection module 1300 may include an amplifier for more accurate detection.

The terahertz wave detecting device 1000 may simultaneously provide a terahertz wave and a light signal having a frequency corresponding to the terahertz wave by using the terahertz wave generating module 1100. The terahertz wave detecting device 1000 may monitor or detect the terahertz wave using the light signal.

Figure 14:
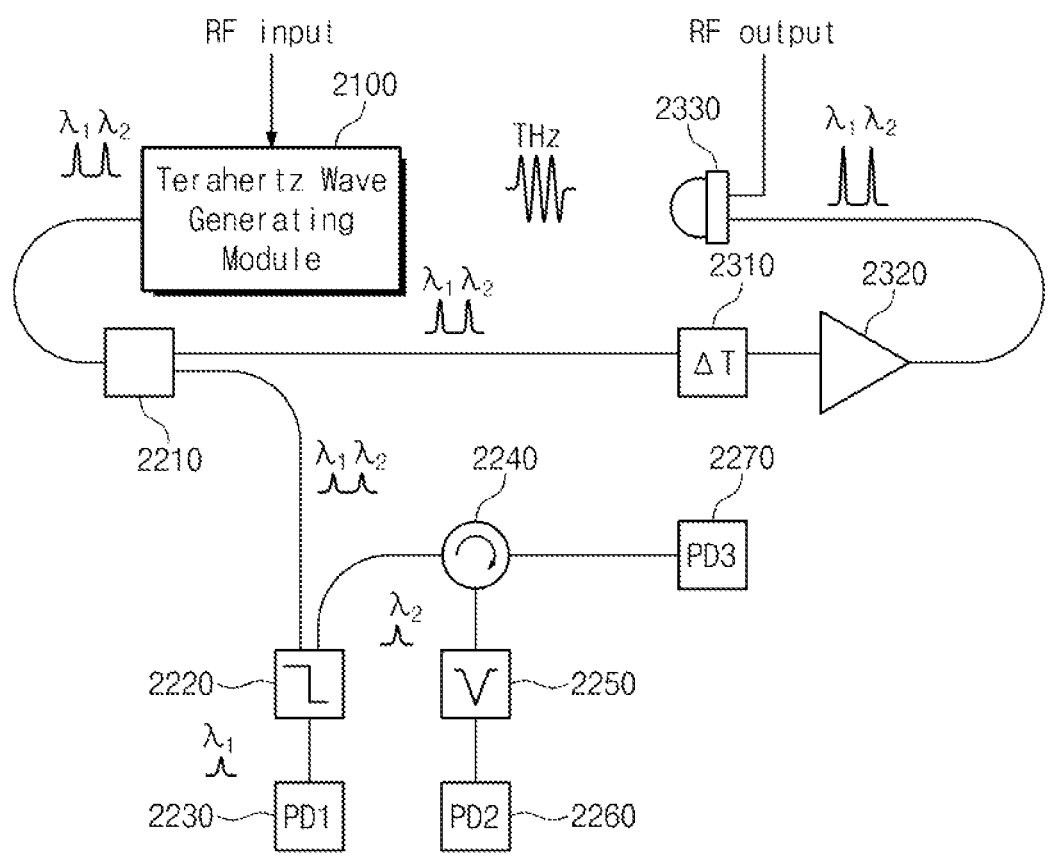
FIG. 14 is a block diagram schematically illustrating a terahertz wave detecting device according to another embodiment of the inventive concept.

FIG. 14 is a block diagram schematically illustrating a terahertz wave detecting device 2000 according to another embodiment of the inventive concept. Referring to FIG. 14, the terahertz wave detecting device 2000 may include a terahertz wave generating module 2100, an optical coupler 2210, a first optical filter 2220, a first optical detector 2230, an optical circulator 2240, a second optical filter 2250, a second optical detector 2260, a third optical detector 2270, an optical delay line 2310, an optical amplifier 2320, and a terahertz wave detector 2330.

The terahertz wave generating module 2100 may simultaneously provide a terahertz wave and a light signal having a frequency corresponding to the terahertz wave by using a bidirectional light source. The light signal provided by the terahertz wave generating module 2100 may be a dual-mode beam having a first wavelength and a second wavelength. The terahertz wave and the light signal provided by the terahertz wave generating module 2100 may be modulated in response to an RF signal provided by an external device. The terahertz wave generated by the terahertz wave generating module 2100 may be output to a target location. The light signal generated by the terahertz wave generating module 2100 may be provided to the optical coupler 2210.

The optical coupler 2210 may separate the light signal generated by the terahertz wave generating module 2100 according to a predetermined ratio. A part of the light signal split by the optical coupler 2210 may be provided for monitoring, and a remaining part may be provided to detect a terahertz wave. For example, the optical coupler 2210 may separate the light signal such that 5% of the light signal split by the optical coupler 2210 is provided for monitoring and 95% thereof is provided to detect a terahertz wave. However, the inventive concept is not limited thereto.

A part of the light signal split by the optical coupler 2210 may be provided to the first optical filter 2220. The first optical filter 2220 may be a filter to detect a first wavelength of the light signal. The first optical filter 2220 may have high transmittance with respect to the first wavelength. The first optical filter 2220 may have high reflectance with respect to the second wavelength. The first optical detector 2230 may detect a light having the first wavelength passing through the first optical filter 2220 to analyze the first wavelength.

A light of the second wavelength reflected by the first optical filter 2220 may be transmitted to the second optical filter 2250 through the optical circulator 2240. The second optical filter 2250 may have a filter characteristic having a predetermined slope. The second optical filter 2250 may reflect a part of the light of the second wavelength and transmit a part thereof.

The second optical detector 2250 may detect a light of the second wavelength passing through the second optical filter 2250. The third optical detector 2270 may detect a light of the second wavelength which is reflected from the second optical filter 2250 and is transmitted through the optical circulator 2240. The second wavelength may be analyzed using detection results of the second and third optical detectors 2260 and 2270.

The remaining light signal separated by the optical coupler 2210 may be provided to the optical delay line 2310. The optical delay line 2310 may delay the input light signal. The optical delay line 2310 may delay the light signal to adjust phases of the light signal and the terahertz wave generated by the terahertz wave generating module 2100.

The optical amplifier 2320 may amplify the light signal delayed by the optical delay line 2310. The optical amplifier 2320 may amplify the light signal for easy detection of the terahertz wave.

The terahertz wave detector 2330 may detect the terahertz wave generated by the terahertz wave generating module 2100 using the light signal amplified by the optical amplifier 2320. The light signal provided to the terahertz wave detector 2330 may have the same phase and wavelength as the terahertz wave, so that the terahertz wave detector 2330 detects the terahertz wave via homodyne detection.

The terahertz wave detecting device 2000 may simultaneously provide a terahertz wave and a light signal having a frequency corresponding to the terahertz wave by using the terahertz wave generating module 2100. The terahertz wave detecting device 2000 may control a wavelength of the terahertz wave by monitoring the terahertz wave using the light signal and back-feeding a monitoring result.

The terahertz wave detecting device 2000 may detect the terahertz wave via homodyne detection using the light signal. Since the terahertz wave detecting device 2000 uses for detection the light signal having the same phase and wavelength as the terahertz wave, it is possible to improve detection accuracy.

Figure 15:
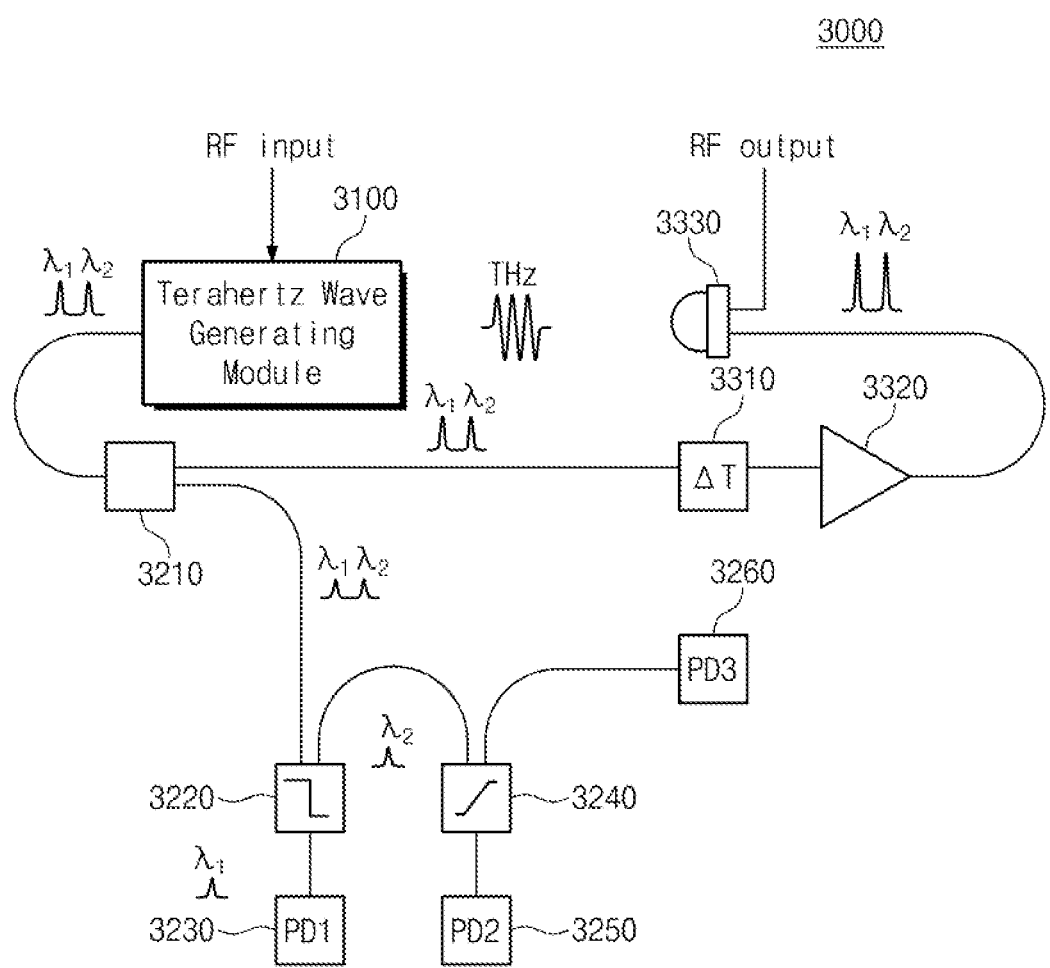
FIG. 15 is a block diagram schematically illustrating a terahertz wave detecting device according to still another embodiment of the inventive concept.

FIG. 15 is a block diagram schematically illustrating a terahertz wave detecting device 3000 according to still another embodiment of the inventive concept. Referring to FIG. 15, the terahertz wave detecting device 3000 may include a second optical filter 3240 having a filter characteristic different from that of FIG. 14. The second optical filter 3240 of the terahertz wave detecting device 3000 may not transmit a first wavelength range of wavelength, so that an optical circulator is not required.

Figure 16:
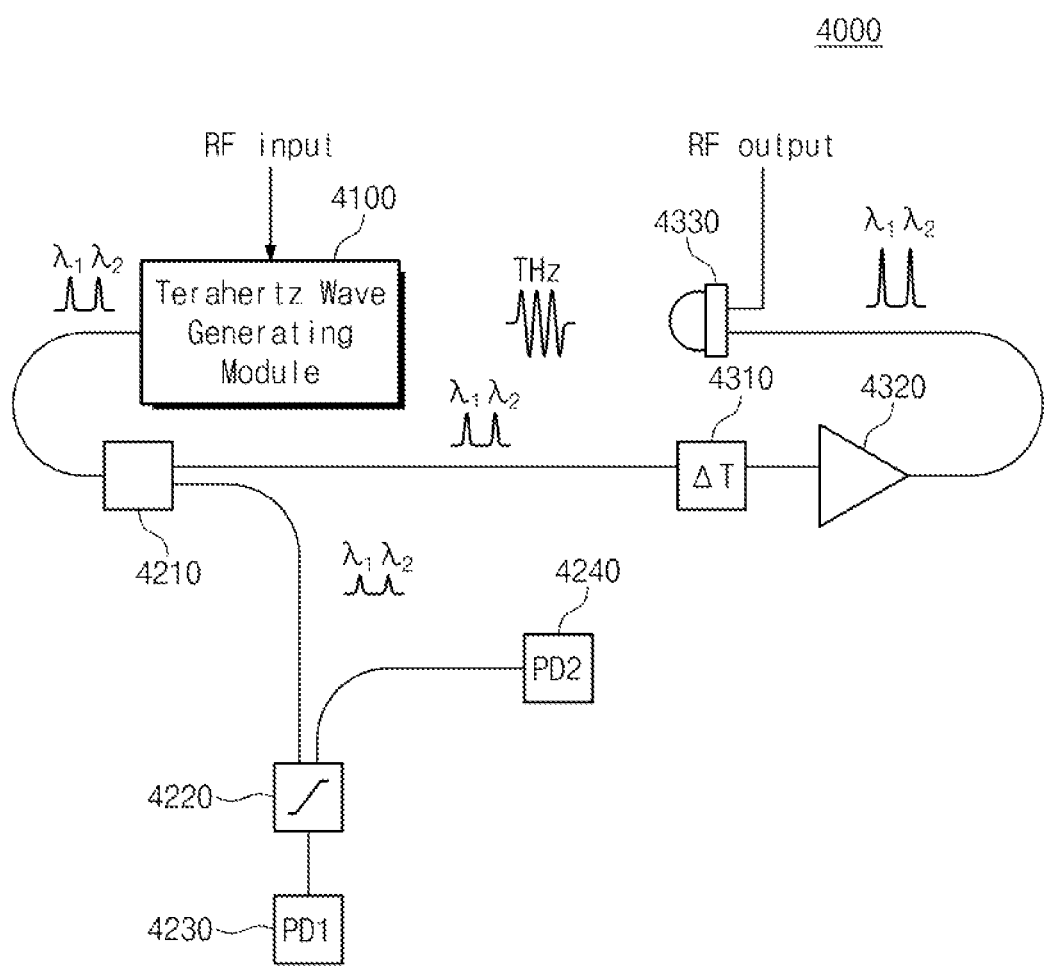
FIG. 16 is a block diagram schematically illustrating a terahertz wave detecting device according to yet another embodiment of the inventive concept.

FIG. 16 is a block diagram schematically illustrating a terahertz wave detecting device 4000 according to still another embodiment of the inventive concept. Referring to FIG. 16, a light signal wavelength analyzing method employed by the terahertz wave detecting device 4000 may be different from that used by the terahertz wave detecting device 2000 of FIG. 14.

A light signal separated by an optical coupler 4210 for monitoring may be provided to an optical filter 4220. The optical filter 4220 may have a transmittance with respect to a second wavelength, the transmittance linearly decreasing with a frequency of the second wavelength and a reflectance with respect to the second wavelength, the reflectance linearly increasing with the frequency of the second wavelength.

A first optical detector 4230 may detect lights of first and second wavelengths passing through the optical filter 4220. A second optical detector 4240 may detect a light of the second wavelength reflected from the optical filter 4220. The first and second wavelengths of a light signal may be analyzed by comparing detection results of the first and second optical detectors 4230 and 4240.

The terahertz wave detecting device 4000 may simultaneously provide a terahertz wave and a light signal having a frequency corresponding to the terahertz wave by using the terahertz wave generating module 4100. The terahertz wave detecting device 4000 may control a wavelength of the terahertz wave by monitoring the terahertz wave using the light signal and back-feeding a monitoring result.

The terahertz wave detecting device 4000 may detect the terahertz wave by homodyne detection using the light signal. Since the terahertz wave detecting device 4000 uses for detection the light signal having the same phase and wavelength as the terahertz wave, it is possible to improve the accuracy of detecting the terahertz wave.

FIGS. 14 to 16 exemplarily illustrate terahertz wave detecting devices using homodyne detection. However, the inventive concept is not limited thereto, and the terahertz wave detecting devices using a terahertz wave generating module of the inventive concept may detect a terahertz wave using a light signal generated by a terahertz wave generating module in a heterodyne manner.

The inventive concept may be variously modified or changed. For example, the detailed structures of the terahertz wave generating module, monitoring module, and detection module may be variously changed or modified according to environmental conditions and use.

While the inventive concept has been described with reference to exemplary embodiments, it will be apparent to those skilled in the art that various changes and modifications may be made without departing from the spirit and scope of the present invention. Therefore, it should be understood that the above embodiments are not limitative, but illustrative.

What is claimed is:

1. A terahertz wave generating module, comprising:
    a bidirectional light source which provides a first dual-mode beam in a first direction and a second dual-mode beam in a second direction;
    a forward lens unit which focuses the first dual-mode beam;
    a photomixer unit which converts the first dual-mode beam focused by the forward lens unit into a terahertz wave;
    a backward lens unit which focuses the second dual-mode beam; and
    a light output unit which uses the second dual-mode beam focused by the backward lens unit as a light signal,
    wherein the bidirectional light source, the forward lens unit, the photomixer unit, the backward lens unit, and the light output unit are integrated in a housing.

2. The terahertz wave generating module of claim 1, wherein a wavelength of the second dual-mode beam is equal to that of the first dual-mode beam.

3. The terahertz wave generating module of claim 1, further comprising:
    an optical isolator located between the bidirectional light source and the forward lens unit and adjusting a propagation direction of the first dual-mode beam in one direction only.

4. The terahertz wave generating module of claim 3, wherein the bidirectional light source, the optical isolator, and the backward lens unit are placed on a support for adjusting a height according to an optical loss.

5. The terahertz wave generating module of claim 4, wherein the support is formed on a metal block including a thermistor for temperature measurement.

6. The terahertz wave generating module of claim 5, wherein the metal block is formed on a temperature pad for adjusting a temperature of the metal block.

7. The terahertz wave generating module of claim 1, wherein the bidirectional light source comprises:
    a first laser bi-directionally outputting a first light of a first wavelength; and a second laser linearly integrated with the first laser and bi-directionally outputting a second light of a second wavelength.

8. The terahertz wave generating module of claim 7, wherein each of the first and second lasers is a DFB (Distributed Feedback) laser and the first and second lasers are integrated and connected with micro heaters for controlling the first and second wavelengths.

9. The terahertz wave generating module of claim 1, further comprising:
a connector providing a high frequency signal to the bidirectional light source, the first dual-mode beam being modulated in response to the high frequency signal.

10. The terahertz wave generating module of claim 1, wherein the forward lens unit comprises:
a first collimation type aspherical lens converting the first dual-mode beam provided from the bidirectional light source into a collimation beam; and
a second collimation type aspherical lens focusing the collimation beam on the photomixer unit.

11. The terahertz wave generating module of claim 1, wherein the forward lens unit comprises:
a focusing type aspherical lens converting the first dual-mode beam provided from the bidirectional light source into a focused beam and focusing the focused beam on the photomixer unit.

12. A terahertz wave generating module, comprising:
a bidirectional light source which provides in a first direction a first dual-mode beam having a first wavelength and a second wavelength and provides in a second direction a first single-mode beam having the first wavelength and a second single-mode beam having the second wavelength;
a forward lens unit which focuses the first dual-mode beam;
a photomixer unit which converts the first dual-mode beam focused by the forward lens unit into a terahertz wave;
a backward lens unit which focuses the first and second single-mode beams; and
an optical detection unit which detects the first and second single-mode beams focused by the backward lens unit,
wherein the bidirectional light source, the forward lens unit, the photomixer unit, the backward lens unit, and the optical detection unit are integrated in a housing.

13. The terahertz wave generating module of claim 12, wherein the bidirectional light source comprises:
a first laser integrated on a first node of a Y-branch type waveguide and bi-directionally outputting the first single-mode beam having the first wavelength; and
a second laser integrated on a second node of the Y-branch type waveguide and bi-directionally outputting the second single-mode beam having the second wavelength,
wherein the first and second single-mode beams are coupled to a third node of the Y-branch type waveguide to be output as the first dual-mode beam.

14. The terahertz wave generating module of claim 13, wherein a Y-branch type waveguide connected with the third node is integrated into two waveguides, the first dual-mode beam being output through the two waveguides.

15. The terahertz wave generating module of claim 12, wherein the optical detection unit comprises:
an optical filter pair filtering the first and second single-mode beams; and
an optical detector pair detecting the first and second single-mode beams filtered.

16. The terahertz wave generating module of claim 12, wherein the photomixer unit comprises:
a photomixer chip including at least one electrode pad and generating a terahertz wave in response to a beam;
a submount including at least one solder pad for supplying electric power to the electrode pad and fixing the photomixer chip;
a coaxial cable connected with the solder pad of the submount;
a photomixer body fixing the photomixer chip, the submount, and the coaxial cable and emitting heat generated from the photomixer chip; and
a silicon lens attached to the photomixer body and controlling a direction of the terahertz wave.

17. The terahertz wave generating module of claim 16, wherein the photomixer chip comprises:
an active layer generating a photocurrent in response to the beam; and
an antenna emitting a terahertz wave in response to the photocurrent.

18. A terahertz wave detecting device, comprising:
a terahertz wave generating module which provides in a first direction a terahertz wave of first and second wavelengths and provides in a second direction a dual-mode light signal corresponding to the terahertz wave, the terahertz wave and the light signal being modulated in response to a high frequency signal;
a monitoring module which monitors the dual-mode light signal; and
a detection module which detects the terahertz wave using the dual-mode light signal.

19. The terahertz wave detecting device of claim 18, wherein the monitoring module comprises:
at least one optical filter having different filter characteristics with respect to the first wavelength and the second wavelength; and
at least one optical detector detecting a light passing through the optical filter to monitor the dual-mode light signal.

20. The terahertz wave detecting device of claim 18, wherein the detection module comprises:
an optical delay line delaying the dual-mode light signal in response to a phase of the terahertz wave;
an optical amplifier amplifying the delayed dual-mode light signal; and
a detector detecting the terahertz wave by homodyne detection using the amplified dual-mode light signal.

* * * * *